United States Patent [19]
Knechtle et al.

[11] Patent Number: 5,762,927
[45] Date of Patent: Jun. 9, 1998

[54] THYMUS TOLERANCE IN PRIMATES

[75] Inventors: Stuart J. Knechtle, Oregon, Wis.; Jue Wang; Jon A. Wolff, both of Madison, Wis.; David M. Neville, Jr., Street-9624 Parkwood Dr., Bethesda, Md. 20814

[73] Assignees: Wisconsin Alumni Research Foundation, Madison, Wis.; David M. Neville, Jr., Bethesda, Md.

[21] Appl. No.: 827,772

[22] Filed: Apr. 11, 1997

Related U.S. Application Data

[63] Continuation of Ser. No. 422,100, Apr. 14, 1995, abandoned, which is a continuation-in-part of Ser. No. 40,681, Mar. 31, 1993, abandoned.

[51] Int. Cl.$^6$ .................... A61K 39/395; A61K 35/12; C07K 16/28
[52] U.S. Cl. .................... 424/93.21; 424/154.1; 424/183.1; 424/534; 530/391.1; 530/391.7; 530/391.9
[58] Field of Search .................... 530/391.1, 391.7, 530/391.9; 424/183.1, 534, 93.21, 154.1

[56] References Cited

U.S. PATENT DOCUMENTS 5,167,956  12/1992  Neville, Jr. .................... 424/85.1

OTHER PUBLICATIONS

Perico, N. et al. Exper. Neph. 1: 120–127, 1993.
Waldmann, H. et al. TiPS 14: 143–148, May 1993.
Pearson, T. C. et al. Transplantation 54: 475–483, Sep. 1992.
Blazar, B. R. et al. J. Immunol. 147: 1492–1503, Sep. 1991.
Barber, W. H. et al. Transplantation 51: 70–75, Jan. 1991.
Barrett, J. T. Basic immunology and its medical application, C. V. Mosby Co., St. Louis, MO, p.48, 1980.
Neville, et al., In vivo T–cell ablation by a holo–immunotoxin directed at human CD3, 89 *Proc. Natl. Acad. Sci. USA* 2585–2589 (1992).
Goss, et al., Donor–Specific Cardiac Allograft Tolerance Without Immunosuppression After Intrathymic Injection of Donor Alloantigen, 24*Transplantation Proceedings*, 2879–2880 (1992).
Posselt, et al., Promotion of Pancreatic Islet Allograft Survival by Intrathymic Transplantation of Bone Marrow, 41 *Diabetes* 771–775 (1992).
Posselt, et al., Induction of Donor–Specific Unresponsiveness by Intrathymic Islet Transplantation, 249 *Science* 1293–1295 (1990).
Ohzato, et al., Tolerance Induction to Skin Allografts Following Intrathymic Injection With Donor–Specific Splenocytes in Major Histocompatibility Complex Class I, Class I+MHS, and Class I+II Disparities, 25 *Transplantation Proceedings*, 297–298 (1993).
Oluwole, et al., Induction of Tolerance to Rat Cardiac Allografts By Intrathymic Donor MHC–Class I Antigen, *Transplantation Immunity and GVH Disease II* Abstract 2723 FASEB (1992).
Knechtle, et al., Induction of Specific Tolerance by Intrathymic Injection of Recipient Muscle Cells Transfected With Donor Class I Major Histocompatibility Complex, 57 *Transplantation*990–996 (1994).
E. Barr et al. (1991) Science 254: 1507–1509.
F. D. Ledley (1991) Human Gene Therapy 2: 77–83.
S. F. Oluwole et al (1992) Fed. Am. Soc. Exp. Biol. (FASEB)J.(1992) 6(4): A 1406, Abstract No. 2723.
E. Ralston et al (1989) J. Cell. Biol. 109: 2345–2352.
J. A. Goss et al. (1992) Transplantation Proceedings 24(6): 2879–2880.
S. F. Oluwole et al (1993) Transplantation Proceedings 25(1): 299–300.
H. Ohzato et al (1993) Transplantation Proceedings 25(1): 297–298.
M. Hoffman (1991) Science 254: 1455–1456.
*Scientific and Technical Aspects of the Major Histocompatibility Complex*, 23–99 (Moulds, et al., Eds., 1989).
R. Billingham, et al., 172 Nature 603–606 (1953).
F. Shapiro, et al., 106 Proc. Soc. Exp. Biol. 472–475 (1961).
L. Brent, et al., 196 Nature 1298–1301 (1962).
G. Gowland, 21 Brit. Med. Bull. 123–128 (1965).
F. Stuart, et al., 160 Science 1463–1465 (1968).
R. Wilson, et al., 7 Transplatation 360–371 (1969).
J. Fabre, et al., 14 Transplantation 608–617 (1972).
P. Caves, et al., 16 Transplantation 252–256 (1973).
J. Little, et al., 19 Transplantation 53–59 (1975).
N. Kamada, et al., 13 Transplant. Proc. 837–841 (1981).
T. Yasumura, et al., 36 Transplantation 603–609 (1983).
K. Wood, et al., 39 Transplantation 56–62 (1985).
N. Kamada, 6 Immunology Today 336–342 (1985).
C. Priestley, et al., 48 Transplantation 1031–1038 (1989).
K. Murphy, et al., 250 Science 1720–1723 (1990).
R. Sumimoto, et al., 50 Transplantation 678–682 (1990).
A. Posselt, et al., 249 Science 1293–1295 (1990).
A. Posselt, et al., 41 Diabetes 771–775 (1992).
Y. Yamaguchi, et al., 21 Transplant. Proc. 3555 (1989).
D. Wray, et al., 53 Transplantation 167–174 (1992).
J. Madsen, et al., 332 Nature 161–164 (1988).
A. Behara, et al., 6 The FASEB Journal 2853–2858 (1992).
M. French, et al., The Lancet 1103–1106 (1969).
C. Rada, et al., 87 Proc. Natl. Acad. Sci. U.S.A. 2167–2171 (1990).
A. Mellor, et al., 36 Cell 139–144 (1984).
J. Fechner, et al., Sep., 1991 meeting paper.

(List continued on next page.)

*Primary Examiner*—Frank C. Eisenschenk
*Assistant Examiner*—Evelyn Rabin
*Attorney, Agent, or Firm*—Quarles & Brady

[57] ABSTRACT

Disclosed is a method of inhibiting a rejection response by a primate to a transplanted organ. One exposes the primate to a mutant diphtheria toxin linked to anti-CD3 antibody so as to largely eliminate the host's peripheral blood T cell lymphocyte population. At the same time as, or after, the exposure step one administers to the primate's thymus gland donor lymphocytes. Transplantation of the organ follows. The primate is tolerized to the transplanted organ.

4 Claims, No Drawings

OTHER PUBLICATIONS

J. Salaün, et al., 247 Science 1471–1474 (1990).
S. Gillis, et al., 120 J. of Immunol. 2027–2032 (1978).
*Tissue Transplantation*, 80–94 (Morris, ed., 1982).
P. Norton, et al., 5 Mol. and Cell. Biol. 281–290 (1985).
J. Van Snick, et al., 83 Proc. Natl. Acad. Sci. U.S.A. 9679–9683 (1986).
P. Felgner, et al., 84 Proc. Natl. Acad. Sci. U.S.A. 7413–7417 (1987).
J. DeWet, et al., 7 Mol. and Cell. Biol. 725–737 (1987).
N. Cohen, et al., 25 Human Immunol. 207–222 (1989).
R. Horton, et al., 77 Gene 61–68 (1989).
E. Barr, et al., 254 Science 1507–1511 (1991).
J. Wang, et al., 53 Transplantation 703–705 (1992).
S. Jiao, et al., 575 Brain Res. 143–147 (1992).
J. Wolf, et al., 247 Science 1465–1468 (1990).
L DeVito, et al., 32 Human Immunol. 125–133 (1991).

THYMUS TOLERANCE IN PRIMATES

This is a continuation of application Ser. No. 08/422,100 filed Apr. 14, 1995, now abandoned, which is a continuation-in-part of Ser. No. 08/040,681 filed Mar. 31, 1993, now abandoned.

FIELD OF THE INVENTION

This invention generally relates to techniques for inducing immunological tolerance in primates. It appears to be especially well suited to provide a method for inhibiting rejection of transplanted organs.

BACKGROUND OF THE INVENTION

Increased success in clinical organ transplantation has paralleled improvements in techniques for immunosuppression. However, increasingly potent immunosuppressant drugs often produce complications due to their lack of specificity. For example, recipients can become very susceptible to infection. Highly specific immunosuppression is therefore desired.

Moreover, the goal is to achieve more than simply delaying the rejection response. Rather, the goal is to inhibit the rejection response to the point that rejection is not a factor in reducing average life span ("tolerization").

One approach to try to achieve such immunosuppression has been to expose the recipient to cells from the donor prior to the transplant, with the hope of inducing tolerance to a later transplant. This approach has involved placement of donor cells (e.g. bone marrow) presenting MHC Class I antigens in the recipient's thymus shortly after application of anti-lymphocyte serum or radiation. However, this approach has proved difficult to adapt to live primates (e.g. monkeys; humans). ALS and/or radiation render the host susceptible to disease or side-effects and/or are insufficiently effective.

In unrelated work, in D. Neville et al., 89 P.N.A.S. USA 2585 (1992) there was described an immunotoxin for T cell ablation for disease control. See also U.S. Pat. No. 5,167,956.

Accordingly, there is a need for a means for imparting tolerance in primates, without the adverse attributes of using ALS or radiation.

SUMMARY OF THE INVENTION

The invention provides a method of inhibiting a rejection response by a primate to a foreign primate donor organ cell. The primate preferably has a functional thymus gland, such as one typically finds in primates that have not yet completed puberty. One exposes the primate to an immunotoxin so as to reduce the primate's peripheral blood T-cell population by at least 80%. The preferred immunotoxin is anti-CD3 antibody linked to a diphtheria protein toxin, wherein the protein has a binding site mutation.

One administers to the thymus gland lymphocytes having MHC Class I antigen of the same haplotype as the MHC of the donor cell. One then transplants the organ cell into the primate. A rejection response by the host to a donor organ cell is inhibited, and the host is tolerized to the donor organ cell.

Preferably, the administered lymphocytes are from the donor, the exposure step reduces the host's own T-lymphocyte peripheral blood population by at least 90%, and the immunotoxin is anti-CD3-CRM9(or a toxin derived therefrom).

For primates, the invention is likely to be most useful where the child is prepubertal, albeit it should have some value at least until the thymus gland has completely involuted. In humans, the method should be most suited for males under 13 and females under 12.

The objects of the invention therefore include providing methods of the above kind for inducing tolerance to transplanted organs. This and still other objects and advantages of the present invention will be apparent from the description which follows.

DESCRIPTION OF THE PREFERRED EMBODIMENTS

Without thymic treatment, rhesus monkey renal allografts reject at a mean of 9 days. Renal allografts in rhesus monkeys (age 2–5 years; 2–3 kg body weight) were performed for the purpose of establishing a model of thymic tolerance in primates. The experimental protocol consisted of first selecting MHC class I disparate rhesus monkey donors and recipients. Donor lymphocytes were injected into the recipient thymus gland 7 days prior to renal allografting from the same donor. Recipients received the immunotoxin of the present invention by intravenous injection. Renal allografts were performed and recipients underwent native nephrectomy.

Immunotoxin

Techniques for preparing anti-CD3-CRM9(where the antibody is directed at the human T-cell receptor complex "CD3") have previously been described. See U.S. Pat. No. 5,167,956 and D. Neville et al., 89 P.N.A.S. USA 2585–2589 (1992). A hybridoma secreting UCHT1 was kindly provided by Dr. Peter Beverly, Imperial Cancer Research Fund, and was grown in ascites fluid and purified over immobilized Protein A. This is an IgG1.

We have more recently prepared a rhesus analog of the above immunotoxin using the anti-rhesus CD3ε monoclonal antibody FN18. (FN18 kindly provided by Dr. Margreet Jonker, Biomedical Primate Research Center, Rijswijk, Netherlands.) F. Nooij et al., 16 Eur. J. Immunol. 981–984 (1986). FN18, also an IgG1, is the rhesus analog of UCHT1 and shares with it the property of being a T-cell mitogen in the presence of mixed mononuclear cells. FN18 was produced in hollow fiber and purified over Protein A. The strain of C. diphtheriae used for production of CRM9, C7 (βh tox-201 tox-9 h') was obtained from R. Holmes, Uniformed Services University of Health Sciences, Bethesda, MD. See also V. Hu et al., 902 Biochimicia et Biophysica Acta 24–30 (1987).

Antibody-CRM9 was recovered from the supernatant of 30 liter fermentation runs under careful control of iron concentration. See S. L. Welkos et al., 37 J. Virol. 936–945 (1981). CRM9 was purified by membrane concentration, ammonium sulfate precipitation and chromatography over DEAE. See S. Carroll et al., 165 Methods In Enzymology 68 (1988).

Large scale purification of immunotoxin was accomplished by HPLC size exclusion chromatography on MODcol (1266 Andes Blvd., St. Louis, Mo. 63132) 2"×10"column packed with ZORBAX® Chromatography Column Bulk packing (DuPont Company) GF-250 5μm, 150 Å. Fractions containing 1:1 toxin:antibody mol ratios were isolated for these studies.

Immunotoxins were synthesized as previously described by thiolating both the monoclonal antibody moiety and the toxin moiety and then crosslinking with bismaleimidohexane. See D. Neville et al., 264 J. Biol. Chem. 14653–14661

(1989). CRM9 was nicked and the monomer (Carroll et al.) was isolated by the MODcol column described above prior to thiolation.

While CRM9 is a preferred mutant diphtheria toxin protein, other diphtheria mutants with a mutation in the DT binding region should also be suitable (as the concept behind the immunotoxin is to replace the normal binding function with the antibody provided T-cell binding function, with minimal conformational change).

T-Cell Ablation

Monoclonal antibody FN18 (specific for rhesus monkey T lymphocytes) coupled to the immunotoxin CRM9 was used to deplete peripheral blood T-cells to levels below 200 cells/$ml^3$ in adult rhesus monkeys (measured six days after the injection). Some modest B cell depletion occurred. Following depletion, complete T-cell recovery takes about three to four weeks in a juvenile rhesus monkey model using this agent. Surprisingly, notwithstanding this fast recovery, donor T-cells injected into the thymus still were not impaired in their ability to tolerize.

Four monkeys received 0.2 mg/kg of immunotoxin, in three divided doses (24 hours apart from each other). Another monkey received 0.133 mg/kg immunotoxin in two divided doses (24 hours apart from each other), and the other monkey received 0.1 mg/kg in two divided doses (24 hours apart from each other). Two days after the last dose of immunotoxin, all monkeys except the last had at least 80% (actually greater than 99%) depletion of T cells both in the peripheral blood and in the lymph nodes. The lowest dose used in the last monkey reduced, but did not substantially eliminate either peripheral blood or lymph node lymphocytes.

Transplants

Table 1 summarizes the outcome of renal transplants performed following thymic injection of donor lymph node lymphocytes (mixture of T and B cells) combined with immunotoxin therapy. Cells injected intrathymically consisted of the pooled axillary and inguinal lymph node lymphocytes in the numbers listed.

TABLE 1

| Monkey # | # Donor Lymphocytes | Interval to Transplant (days) | Anti-CD3-CRM9 Lymphoablative Therapy(mg/kg) | Graft Survival (days) | Cause of Failure |
|---|---|---|---|---|---|
| 92099 | $1.6 \times 10^8$ | 7 | 0.20 | 8 | Urine leak |
| 93023 | $7.0 \times 10^8$ | 7 | 0.20 | >180 | |
| 92049 | $1.4 \times 10^8$ | 7 | 0.20 | 13 | Pneumonia |
| 93038 | $1.6 \times 10^8$ | 0 | 0.133 | 39 | Pneumonia |
| 92102 | $0.14 \times 10^8$ | 0 | 0.10 | 9 | Rejection |
| 92108 | $1.88 \times 10^8$ | 7 | 0.20 | >43 | |

Two monkeys died of pneumonia, one at 39 days and the other at 13 days. A third monkey died at 8 days of complications stemming from a urine leak. At autopsy, none of these three monkeys had any evidence of renal transplant rejection, either grossly or histologically.

Monkey #93023, which received the intrathymic injection and immunotoxin seven days prior to renal transplantation, had normal renal function more than 180 days post-transplant. A renal biopsy of his transplanted kidney at 100 days showed no evidence of rejection.

Surgical Procedures

Preferred surgical procedures included partial median sternotomy for exposure of the thymus and injection of donor lymphocytes into the thymus gland; inguinal and axillary lymphadenectomy to procure donor lymphocytes; laparotomy for procurement of the left kidney from kidney donors; and a second laparotomy for renal transplantation and native right nephrectomy. All of these procedures will be performed under general anesthesia as outlined below. Serial blood draws will be performed under ketamine and xylazine anesthesia as outlined below.

Thymic injection is performed through a midline chest incision beginning at the sternal notch extending down to the midportion of the sternum. The sternum is divided and retracted to expose the underlying thymus gland. The thymus gland is injected with donor lymphocytes and the sternum reapproximated and the soft tissue closed.

Donor nephrectomy is performed under general anesthesia through an upper midline incision in the abdomen. The retroperitoneal attachments of the left kidney are divided, the ureter is ligated and divided near the bladder, and the left renal artery and vein are dissected free. The left renal artery and vein are ligated adjacent to the aorta and inferior vena cava, and the kidney excised and flushed on the back table with preservation solution.

The recipient operation for renal transplantation is performed by making a midline abdominal incision under general anesthesia. The distal aorta and inferior vena cava are dissected free. The vena cava is clamped proximally and distally near its bifurcation and the donor renal vein anastomosed end-to-side to the recipient inferior vena cava using running 7-0 prolene suture. The aorta is cross-clamped proximally and distally just proximal to its bifurcation and the donor renal artery anastomosed end-to-side to the aorta using running 8-0 prolene. A ureteroneocystostomy is then performed by making an anterior cystotomy and anastomosing the spatulated tip of the donor ureter to the bladder mucosa using 8-0 prolene suture. The cystotomy is then closed. The abdomen is then closed.

Lymphadenectomy is performed through an approximately 2 cm groin incision for inguinal lymphadenectomy and a similar length incision for axillary lymphadenectomy. The lymph nodes are excised and bleeding points cauterized. The skin is then closed with running 4-0 nylon suture.

It should be appreciated that kidney transplants are merely an example application. The invention should be suitable for use with a wide variety of organs (e.g. liver, heart, lung).

Lymphocytes

Lymphocytes to be donated are preferably pooled from axillary and cervical lymph nodes of a single donor. The nodes are harvested, strained through a mesh to separate the lymphocytes, diluted with saline, and then injected. However, instead, a representative "cocktail" of lymphocytes from several primates other than the donor, at least one of which turns out to be the same haplotype as the likely donor, should also work (if the donor is not available early enough).

Other Considerations

For humans, the preferred doses of the immunotoxin are those sufficient to deplete peripheral blood T-cell levels to 80%, preferably 90% (or especially preferably 99%) of preinjection levels. This should require mg/kg levels for humans similar to those for monkeys (e.g. 0.15 mg/kg to 0.2 mg/kg body weight), which toxicity studies indicate should be well tolerated by humans.

The immunotoxin injection should preferably be made within a week or two prior to the donor cell treatment (albeit there are indications from murine and in vitro studies that even simultaneous application may suffice).

In sum, surprisingly immunotoxins known to severely deplete T-lymphocytes will selectively deplete the host lymphocytes, without interfering with the donor T-lymphocytes ability to cause tolerization. Further, the extreme level of depletion caused by this immunotoxin facilitates tolerization.

It will be appreciated that the above disclosure relates only to the preferred embodiments. The invention is not so limited. For the full scope of the invention, the claims should be looked to.

We claim:

1. A method of inhibiting a rejection response by a primate to a foreign mammalian organ cell from a donor, wherein the primate has a thymus gland, comprising the steps of:

exposing the primate to an immunotoxin so as to reduce the primate's peripheral blood T-cell lymphocyte population by at least 80%, wherein the immunotoxin is anti-CD3 antibody linked to a diphtheria protein toxin, wherein the protein has a binding site mutation;

administering, within two weeks after but not before the exposure step, lymph node lymphocytes to the thymus gland, the lymph node lymphocytes being from said donor having MHC Class I antigen of the same haplotype as of the MHC of the donor organ cell; and then transplanting the organ cell into the primate;

whereby a rejection response by the primate to the donor organ cell is reduced and the primate is tolerized to the donor cell.

2. The method of claim 1, wherein the primate has not yet completed puberty at the time of the administering step.

3. The method of claim 2, wherein the exposure step reduces the host's own T-lymphocyte population in peripheral blood by at least 90%.

4. The method of claim 3, wherein the immunotoxin is anti-CD3-CRM9.

* * * * *